United States Patent [19]

Crawford

[11] 4,321,196

[45] Mar. 23, 1982

[54] BIS-ESTERS OF METHANEDIOL WITH ACETONIDES OF AMPICILLIN OR AMOXICILLIN AND PENICILLANIC ACID 1,1-DIOXIDE

[75] Inventor: Thomas C. Crawford, Gales Ferry, Conn.

[73] Assignee: Pfizer Inc., New York, N.Y.

[21] Appl. No.: 246,504

[22] Filed: Mar. 23, 1981

[51] Int. Cl.$^3$ ............................................. C07D 499/80
[52] U.S. Cl. .................................. 260/239.1; 424/271
[58] Field of Search ....................... 260/239.1; 424/271

[56] References Cited

U.S. PATENT DOCUMENTS

| | | | |
|---|---|---|---|
| 3,198,804 | 8/1965 | Johnson et al. | 260/306.7 |
| 3,954,735 | 5/1976 | von Daehne | 260/239.1 |
| 4,185,015 | 1/1980 | Sleezer et al. | 260/239.1 |
| 4,244,951 | 1/1981 | Bigham | 424/250 |

FOREIGN PATENT DOCUMENTS 2044255 10/1980 United Kingdom .

OTHER PUBLICATIONS

Handcastle et al., J. Org. Chem. 31, pp. 897–899 (1966).
Long et al., J. Chem. Soc. (C), pp. 1920–1922 (1971).

*Primary Examiner*—Natalie Trousof
*Assistant Examiner*—Vera C. Clarke
*Attorney, Agent, or Firm*—Charles J. Knuth; Albert E. Frost; Peter C. Richardson

[57] ABSTRACT

Bis-esters of methanediol wherein one hydroxy group of the methanediol is esterified with the carboxy group of hetacillin (or of the p-hydroxy analog of hetacillin) and the other hydroxy group of the methanediol is esterified with penicillanic acid 1,1-dioxide. These orally effective compounds have a particularly broad spectrum of antibacterial activity in mammals, and have an unusually long serum half-life.

3 Claims, No Drawings

BIS-ESTERS OF METHANEDIOL WITH ACETONIDES OF AMPICILLIN OR AMOXICILLIN AND PENICILLANIC ACID 1,1-DIOXIDE

BACKGROUND OF THE INVENTION

This invention relates to bis-esters of methanediol wherein one of the hydroxy groups of the methanediol is esterified with hetacillin (or the p-hydroxy analog thereof), and the other hydroxy group of the methanediol is esterified with penicillanic acid 1,1-dioxide. These compounds have particular value in mammals as oral antibacterial agents against penicillinase producing bacteria. They are efficiently absorbed from the gastrointestinal tract. After absorption they are transformed, providing unusually long-lasting serum levels of ampicillin/amoxicillin and penicillanic acid 1,1-dioxide. By its penicillinase inhibitory activity, the latter enhances the activity of the former against penicillinase producing bacteria.

The present compounds are acetonide derivatives of compounds earlier described in British patent application Ser. No. 2,044,255 and U.S. Pat. No. 4,244,951. Unexpectedly the present compounds show a greatly increased serum half-life of ampicillin/amoxicillin and penicillanic acid 1,1-dioxide in comparison to the parent compounds disclosed in these references.

Hetacillin (and the p-hydroxy analog thereof) have been described in the literature [Handcastle et al., J. Org. Chem. 31, pp. 897–899 (1966); Long et al., J. Chem. Soc. (C); pp. 1920–1922 (1971)]. Esters of hetacillin (and of the p-hydroxy analog thereof) have also been reported as especially usable for oral administration (von Daehne, U.S. Pat. No. 3,954,735, see also Sleezer et al., U.S. Pat. No. 4,185,015), but these compounds are not known to be beta-lactamase inhibitors.

SUMMARY OF THE INVENTION

This invention relates to systemic broad spectrum antibacterial agents of the formula

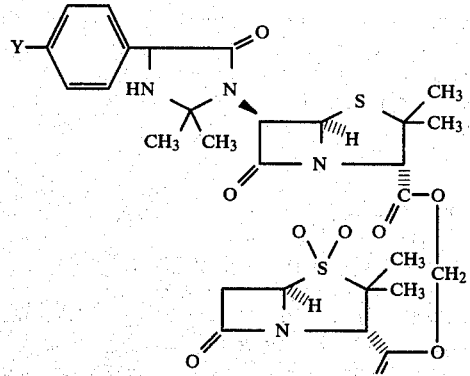

(I)

and the pharmaceutically-acceptable acid addition salts thereof, wherein Y is H or OH and the imidazolidinone side chain is derived from the D-form of alpha-amino phenylacetic acid. When Y is H, the compound is the bis-ester of hetacillin (acetonide of ampicillin) and penicillanic acid 1,1-dioxide with methanediol. When Y is OH, the compound is the bis-ester of the acetonide of amoxicillin and penicillanic acid 1,1-dioxide. The expression "pharmaceutically-acceptable acid addition salts" is intended to encompass such acids as hydrochloric, sulfuric, phosphoric, maleic, succinic, citric, methanesulfonic, p-toluenesulfonic, etc.

Alternative methods for the preparation of the compounds of the present invention are detailed herein. Because it is direct and provides high yields, the preferred process is the reaction of acetone with the methanediol bis-ester of ampicillin (or amoxicillin) and penicillanic acid 1,1-dioxide. This process is the subject of a concurrently filed application entitled "Process for the Bis-esters of Methanediol with the Acetonides of Ampicillin or Amoxicillin and Penicillanic Acid 1,1-Dioxide." by Sklavounos, application Ser. No. 246,503, filed Mar. 23, 1981. A second alternative process for the compounds of the present invention is, in part, the subject of a second concurrently filed application entitled "Improved Process for the Preparation of Penicillanic Acid Esters" by Jasys, application Ser. No. 246,482, filed Mar. 23, 1981.

The invention also encompasses a method of treating susceptible bacterial infections in mammals with the compound alone, in admixture with other antibacterial substances and/or pharmaceutically-acceptable carriers or diluents. The preferred route of administration of the present compounds is oral, since they are efficiently absorbed from the gastrointestinal tract of mammals. After absorption, they are transformed into ampicillin (or amoxicillin) and penicillanic acid 1,1-dioxide, and an extended serum half-life of these compounds results.

DETAILED DESCRIPTION OF THE INVENTION

The imidazolidinone compounds of the present invention are readily prepared by a number of alternative methods.

The preferred method is as follows:

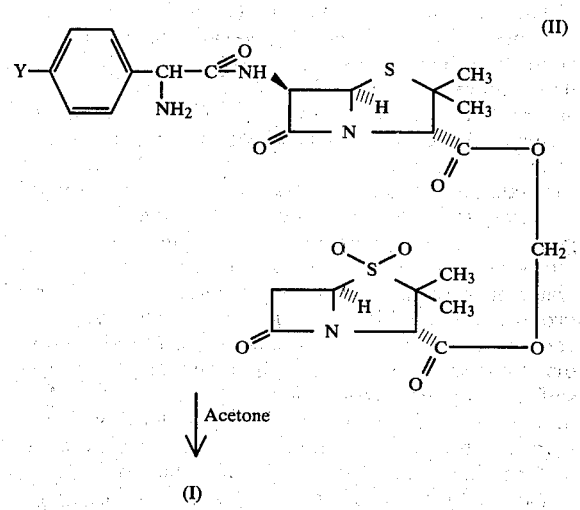

Compounds of the formula (II) are simply allowed to stand in acetone until the reaction is substantially complete, and the excess acetone is removed by evaporation. As the source of the acetone bridge, an acetone ketal (e.g. 2,2-dimethoxypropane) or an enol ether or ester derivative of acetone (e.g. 2-methoxypropene or 2-acetoxypropene) can be used, provided an acid catalyst is present. Temperature is not critical, 0°–50° C.

being fully satisfactory; conveniently, ambient temperatures can be used.

In a second method, the compounds of formula I are prepared by reacting a carboxylate salt of the formula

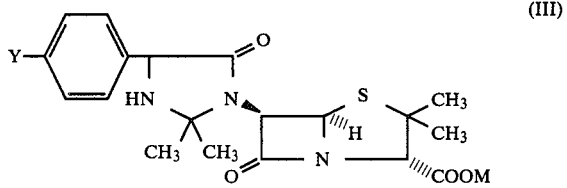
(III)

with a compound of the formula

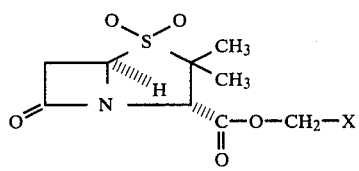
(IV)

wherein Y is as previously defined, M is a carboxylate salt forming cation, and X is a good leaving group, for example, chloro, bromo, iodo, ($C_1$-$C_4$)alkylsulfonyloxy, benzenesulfonyloxy or toluenesulfonyloxy. A variety of cations can be used to form the caboxylate salt in the compound of formula III, but salts which are commonly used include: alkali metal salts, such as sodium and potassium salts; alkaline earth metal salts, such as calcium and barium salts; tertiary amine salts, such as trimethylamine, triethylamine, tributylamine, diisopropylethylamine, N-methylmorpholine, N-methylpiperidine, N-methylpyrrolidine, N,N'-dimethylpiperazine and 1,2,3,4-tetrahydroquinoline; and more recently, quaternary ammonium salts, such as the tetrabutylammonium salt, as disclosed in the concurrently filed patent application by Jasys referenced above.

The reaction between a compound of formula III and a compound of formula IV is usually carried out by contacting the reagents in a polar, organic solvent, at a temperature in the range from about 0° to about 80° C., and preferably from 25° to 50° C. The compounds of formula III and IV are usually contacted in substantially equimolar proportions, by an excess of either reagent, for example up to a ten-fold excess, can be used. A wide variety of solvents can be used, but it is usually advantageous to use a relatively polar solvent, since this has the effect of speeding up the reaction. Solvents, such as water or methanol, which can solvolyze the acetonide group are preferably avoided. Typical solvents which can be used include N,N-dimethylformamide, N,N-dimethylacetamide, N-methylpyrrolidone, dimethylsulfoxide, hexamethylphosphoramide and acetone. The latter is the preferred solvent when a quaternary ammonium salt is used in the preparation of the present compounds. The reaction time varies according to a number of factors, but at about 25° C. reaction times of several hours, e.g. 12 to 24 hours, are commonly used. When X is chloro or bromo, it is sometimes advantageous to add up to about one molar equivalent of an alkali metal iodide, which has the effect of speeding up the reaction.

The compound of formula I is isolated in conventional fashion. When a water-miscible solvent is used, it is usually sufficient simply to dilute the reaction medium with a water immiscible solvent. The diluted reaction mixture is extracted with brine and with water, dried, and the product recovered by solvent evaporation. When a water immiscible solvent is used, it is usually sufficient to omit the dilution step.

A variation of the foregoing method of preparing a compound of formula I involves reaction of a compound of the formula

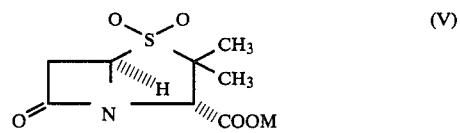
(V)

with a compound of the formula

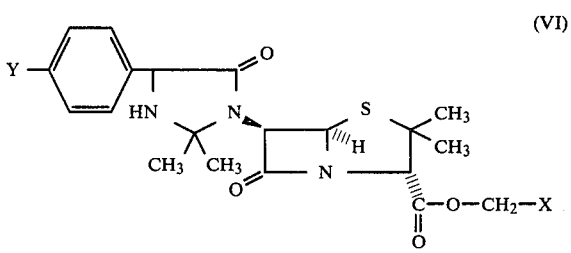
(VI)

wherein M and X are as defined previously. The reaction conditions for the reaction of (V) and (VI) are as described above for the reaction of (III) and (IV).

The compounds of formula III are known antibiotics, which are prepared by the published procedures.

The compounds of formula IV are prepared from the compounds of formula V by reaction with a compound of formula X—$CH_2$—X', wherein X and X' are each good leaving groups, e.g. chloro, bromo, iodo, alkylsulfonyloxy, benenesulfonyloxy, toluenesulfonyloxy or chlorosulfonyloxy. The same conditions that were described previously for reaction of a compound of formula III with a compound of formula V are used for this reaction, except that it is preferable to use an excess of the compound of formula X—$CH_2$—X' (e.g. a four-fold excess).

In like manner, the compounds of formula VI are prepared by reaction of a compound of formula III with a compound of formula X—$CH_2$—X', wherein X and X' are as previously defined. The conditions used are the same as those described previously for reaction of a compound of formula V with a compound of formula X—$CH_2$—X'.

The compounds of the present invention (formula I) are hydrolyzed in aqueous systems to compounds of the formula II. Thus, the alternative routes to formula I compounds described above also provide an alternative synthetic route to the compounds of the formula II.

The pharmaceutically acceptable acid addition salts of the compounds of the present invention are prepared by reaction of the free base form with a molar equivalent of the acid, such as those defined above, in a reaction-inert solvent (i.e. one which will not lead to hydrolysis or solvolysis of either the acetonide or the methanediol bis-ester). Acetone is particularly well-suited as solvent for this purpose. When the salt does not precipitate directly, it is isolated by concentration and/or the addition of a non-solvent such as hexane or ether.

The compounds of formula I possess in vivo anti-bacterial activity in mammals, and this activity can be demonstrated by standard techniques for penicillin compounds. For example, the compound of formula I is administered to mice in which acute infections have been established by intraperitoneal inoculation with a standardized culture of pathogenic bacterium. Infection severity is standardized such that the mice receive one to ten times the $LD_{100}$ ($LD_{100}$: the minimum inoculation required to consistently kill 100 percent of control mice. At the end of the test, the activity of the compound is assessed by counting the number of survivors which have been challenged by the bacterium and also have received the compound of formula I. The compounds of formula I can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects. A compound of formula I breaks down into ampicillin (or amoxicillin) and penicillanic acid 1,1-dioxide after administration to a mammalian subject by both the oral and parenteral route. Penicillanic acid 1,1-dioxide then functions as a beta-lactamase inhibitor and it increases the antibacterial effectiveness of the ampicillin (or amoxicillin), for example, against penicillinase producing strains of *Staphylococcus aureus* or *Escherichia coli*.

In determining whether a particular strain of *Staphylococcus aureus* or *Escherichia coli* is sensitive to a compound of the formula I, the in vivo test described earlier can be used. Alternatively, the minimum inhibitory concentration (MIC) of a 1:1 mixture of ampicillin (or amoxicillin) and penicillanic acid 1,1-dioxide can be measured. The MIC's can be measured by the procedure recommended by the International Collaborative Study on Antibiotic Sensitivity Testing (Ericcson and Sherris, *Acta. Pathologica et Microbiologia* Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

Since the object of the present invention is to provide a single well-absorbed source of ampicillin/amoxicillin and penicillanic acid 1,1-dioxide in serum, the compounds of the present invention are also evaluated by determination of the serum levels of these derived compounds in experimental animals, such as laboratory rats. The serum level results in fasted rats following the oral administration of 20 mg./kg. of 6'-(2,2-dimethyl-4-phenyl-5-imidazolidinon-1-yl)-penicillanoyloxymethyl penicillanate 1,1-dioxide (I, Y=H) are shown in Table I. In this test, 6'-(2-amino-2-phenylacetamido)penicillanoyloxymethyl penicillanate 1,1-dioxide (II, Y=H) at the same oral dosage has been used as control. The blood level of ampicillin was determined by standard plate bioassay methods, using *Sarcina lutea* 07A001 on Seed agar. For determination of penicillanic acid 1,1-dioxide, *Pasturella* 59B010 on MH agar was employed. It will be noted there is an approximately 50% improvement in the half-life of Compound I (Y=H) over Compound II (Y=H).

TABLE I

| | Serum Levels (mcg/ml) Following 20 mg/kg Oral Dosage in Fasted Rats | | | |
|---|---|---|---|---|
| | Compound I (Y = H) | | Compound II (Y = H) | |
| Time (min.) | Ampicillin | Penicillanic Acid 1,1-Dioxide | Ampicillin | Penicillanic Acid 1,1-Dioxide |
| 15 | 1.46 | 1.04 | 3.01 | 1.80 |
| 30 | 1.42 | 1.27 | 2.60 | 2.07 |
| 60 | 0.88 | 0.75 | 1.09 | 0.62 |
| 90 | 0.57 | 0.40 | 0.50 | 0.16 |
| 120 | 0.45 | 0.24 | 0.35 | 0.09 |
| 180 | 0.26 | 0.14 | 0.14 | 0.04 |
| 240 | 0.11 | 0.06 | 0.06 | 0.03 |
| Half-life (min.) | 60.7 | 49.1 | 39.25 | 35.60 |

When using an antibacterial compound of this invention in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the preferred oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally and parenterally at dosages in the range from about 5 to about 100 mg. per kilogram of body weight per day, usually in divided doses. In some instances it may be necessary to use doses outside these ranges.

The present invention is illustrated by the following example. However, it should be understood that the invention is not limited to the specific details of this example.

EXAMPLE

6'-(2,2-Dimethyl-4-phenyl-5-imidazolidinon-1-yl)-penicillanoyloxymethyl Penicillanate 1,1-Dioxide (I, Y=H)

Method A

6'-(2-Amino-2-phenylacetamido)penicillanoyloxymethyl penicillanate 1,1-dioxide (II, Y=H; 594 mg., 1 mmole) as stirred in 30 ml. of acetone at room temperature. After 66 hours the reaction mixture was evaporated to dryness in vacuo, providing an essentially quantitative yield of the title product [m.p. 115–125 (dec); pnmr (CDCl$_3$)delta 1.3–1.7 (18H; three pairs of gem-dimethyl groups), 3.4 (2H; C-6 CH$_2$) 4.2–4.7 (5H; C-3, C-7, C-3', C-6' and C-7' CH), 5.5 (1H, side chain CH), 5.8 (2H, -OCH$_2$O-) and 2.3 (5H, aromatics) ppm].

Under the same conditions 6'-[2-amino-2-(p-hydroxyphenyl)acetamido]penicillanoyloxymethyl penicillanate 1,1-dioxide (II, Y=OH) is converted to 6'-[2,2-dimethyl-4-(p-hydroxyphenyl)-5-imidazolidinon-1-yl]penicillanoyloxymethyl penicillanate 1,1-dioxide (I, Y=OH).

Method B

Hetacillin (III, Y=M=H; 0.60 g., 1.54 mmoles) is combined with 5 ml. of dimethylformamide and then with triethylamine (0.33 ml., 2.5 mmoles), and stirred for 20 minutes. To the resulting homogeneous solution is added chloromethyl penicillanate 1,1-dioxide (IV, X=Cl; Belgian Pat. No. 883,299; 0.433 g., 1.54 mmole). The reaction mixture is then stirred for 5.5 hours at room temperature and then diluted with 100 ml. of ethyl acetate, extracted in sequence with 50 ml. of brine, 50 ml. of water and 50 ml. of brine, dried over anhydrous sodium sulfate, filtered and evaporated to yield the title product, incompletely pure, as an oil. Proton nmr indicated the major presence of the title product.

Method C

Potassium hetacillin (III, Y=H, M=K; 214 mg., 0.5 mmole) was suspended in 5 ml. of dimethylformamide. Iodomethyl penicillanate 1,1-dioxide (IV, X=I; Belgian Pat. No. 883,299; 187 mg., 0.5 mmole) was added in one portion. The reaction mixture was stirred for 1.5 hours at room temperature (by which time complete dissolution occurred), then quenched with 100 ml. of ethyl acetate, and extracted in sequence with 50 ml. of brine, 50 ml. of water and 50 ml. of brine. The organic phase was dried over anhydrous magnesium sulfate and the solvent removed in vacuo. The resulting oily residue was dried under a stream of dry nitrogen to yield the title product as a dry powder (190 mg., 60%), identified by the identity of its pnmr and tlc mobility (silica gel, 95:5 methylene chloride:methanol, phosphomolybdic spray/heat) to that of the same product prepared by Method A above.

I claim:

1. A compound of the formula

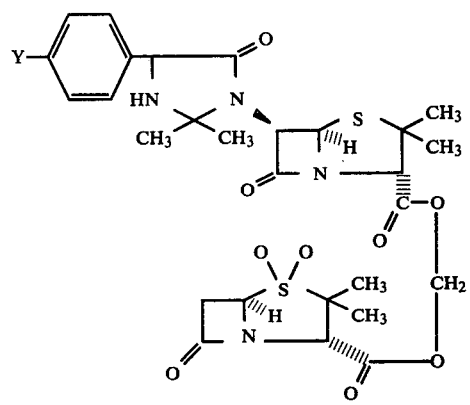

wherein Y is H or OH, and the imidazolidinone sidechain is derived from the D-form of alpha-aminophenylacetic acid; and the pharmaceutically acceptable acid addition salts thereof.

2. The compound of claim 1 wherein Y is H.
3. The compound of claim 1 wherein Y is OH.

* * * * *